United States Patent [19]

Mittelbach et al.

[11] Patent Number: 5,849,939
[45] Date of Patent: *Dec. 15, 1998

[54] METHOD FOR THE PREPARATION OF FATTY ACID ALKYL ESTERS

[75] Inventors: Martin Mittelbach, Am Blumenhang 27, A-8010 Graz; Michael Koncar, Forstgasse 8, A-8501 Lieboch, both of Austria

[73] Assignees: Martin Mittelbach, Graz; Michael Koncar, Lieboch; Vogel & Noot Industrieanlagenbau Gesellschaft m.b.H., Graz, all of Austria

[ * ] Notice: This patent issued on a continued prosecution application filed under 37 CFR 1.53(d), and is subject to the twenty year patent term provisions of 35 U.S.C. 154(a)(2).

[21] Appl. No.: 553,676

[22] PCT Filed: Jul. 8, 1994

[86] PCT No.: PCT/AT94/00088

§ 371 Date: Feb. 27, 1996

§ 102(e) Date: Feb. 27, 1996

[87] PCT Pub. No.: WO95/02661

PCT Pub. Date: Jan. 26, 1995

[30] Foreign Application Priority Data

Jul. 14, 1993 [AT] Austria ..................................... 1399/93

[51] Int. Cl.$^6$ ....................................................... C11C 3/10
[52] U.S. Cl. ........................... 554/169; 554/161; 554/163
[58] Field of Search ................................... 554/169, 161, 554/163

[56] References Cited

FOREIGN PATENT DOCUMENTS

| | | |
|---|---|---|
| 0 131 991 | 1/1985 | European Pat. Off. . |
| 0 591 019 | 4/1994 | European Pat. Off. . |
| 2696185 | 4/1994 | France . |
| AT 392 977 | 7/1991 | Germany . |
| WO 93/09212 | 5/1993 | WIPO . |

OTHER PUBLICATIONS

R.C.A. Lago et al., Extraction and transesterification . . . , Oleagineux, vol. 40, No. 3, Mar. 1985, pp. 147–151.

*Primary Examiner*—Gary Geist
*Assistant Examiner*—Deborah D. Carr
*Attorney, Agent, or Firm*—Birch, Stewart, Kolasch & Birch LLP

[57] ABSTRACT

A method for the preparation of fatty acid alkyl esters by transesterification, in particular catalytic transesterification, of triglycerides, wherein from a reaction mixture, in which the transesterification is carried out, an ester phase and a glycerol phase containing fatty acids, fatty acid salts and/or other fatty acid compounds are formed, which are separated from each other, characterized in that the fatty acids, the fatty acid salts and/or other fatty acid compounds are separated from the glycerol phase, esterified with an alcohol and recycled to a different reaction mixture, in which a further transesterification is carried out. The method according to the invention allows for a transesterification with a high yield of fatty acid esters.

13 Claims, No Drawings

METHOD FOR THE PREPARATION OF FATTY ACID ALKYL ESTERS

This application is a 371 of PCT/AT94/00088 filed Jul. 8, 1994.

BACKGROUND OF THE INVENTION

The invention relates to a method for the preparation of fatty acid alkyl esters by transesterification, in particular catalytic transesterification, of triglycerides, wherein from a reaction mixture, in which the transesterification is carried out, an ester phase and a glycerol phase containing fatty acids, fatty acid salts and/or other fatty acid compounds are formed, which are separated from each other.

By transesterification the alcoholysis of triglycerides is to be understood, i.e. the reaction with alcohols, in particular methanol and ethanol, the monoesters of the fatty acids as well as glycerol forming via the intermediate products di- and monoglycerides.

DESCRIPTION OF CONVENTIONAL ART

Fatty acid esters, in particular the methyl esters, are important intermediate products in oleochemistry. In Europe alone, 200,000 tons of vegetable oil methyl ester are produced annually as raw materials primarily for surfactants. Beside this, the fatty acid methyl ester is of increasing importance as a substitute fuel for diesel fuel.

As the catalysts for the transesterification, basic catalysts (alkali hydroxides, alcoholates, oxides, carbonates, anion exchangers), acidic catalysts (mineral acids, p-toluene sulfonic acid, boron trifluoride, cation exchangers) and enzymes (lipases) may be used. Today catalysts which are soluble in the reaction mixture are preferably used. They form a homogenous mixture and guarantee fast reaction rates and mild reaction conditions. The homogenous catalysts most frequently used are sodium and potassium hydroxide as well as sodium methylate, which, dissolved in alcohol, are admixed to the vegetable oil. Such a method is known from AT-B 386 222. The acidic catalysis requires higher reaction temperatures and pressures and a more complex reaction procedure. An acidic transesterification is known from FR-A-85 02340.

Transesterification with basic catalysis is carried out without the use of a solvent. The reaction starts with a two-phase system of triglyceride and alcohol, yet during reaction progress and the formation of ester, a homogenous phase forms, which turns into two phases again by the formation and separation of glycerol.

In the alcoholysis of triglycerides for the preparation of esters of fatty acids with monohydric alcohols, a phase rich in glycerol is obtained as a by-product. This phase further contains fatty acids, fatty acid salts and fatty acid esters. In order to separate these fatty acid compounds from the glycerol phase, it is generally treated with acids. By this treatment, the fatty acids are set free from the fatty acid salts. The fatty acids as well as the fatty acid esters themselves are not mixable with glycerol and therefore settle as a separate phase from the glycerol phase.

So far, there has not been demonstrated any reasonable use of this fatty acid phase, this phase generally being accepted in the art as a loss from the transesterification process. This loss has a negative effect particularly when the process is carried out on a large scale, where an improvement in the order of 1–2% already increases decisively the economy of the process.

SUMMARY OF THE INVENTION

It is the object of the invention to provide an improved method for the preparation of fatty acid alkyl esters by transesterification, in particular catalytic transesterification, of triglycerides.

The method according to the invention is characterized in that the fatty acids, the fatty acid salts und/or other fatty acid compounds are separated from the glycerol phase, esterified with an alcohol and recycled to a different or further reaction mixture, in which a further transesterification is carried out.

The esterification may be carried out according to known methods, being particularly suitable an esterification with an acidic catalyst. As an example, an acidic catalysis with sulfuric acid, para-toluene sulfonic acid or with ion exchangers in the form of $H^+$ is mentioned.

An esterification of free fatty acids is known from EP-A-0 184 740. Yet this method is a pre-esterification of free fatty acids contained in some naturally ocurring fats and oils. Starting from natural fats and oils containing free fatty acids, fatty acid methyl esters may be obtained by first esterifying the free fatty acids present in the starting material in the presence of acidic catalysts with excess methanol, separating an alcohol phase containing the catalyst, extracting the remaining oil phase (triglyceride phase) with a glycerol-methanol mixture and subjecting the treated oil phase to an alkali-catalyzed transesterification with methanol. It has been shown, however, that also in the alcoholysis of the triglycerides, fatty acid compounds are withdrawn with the glycerol phase from the transesterification process, thus reducing the yield. By the esterification of the fatty acid phase obtained subsequent to transesterification and processing of the glycerol phase, carried out according to the invention, not only the free fatty acids present in the processed triglyceride are included and processed to form fatty acid esters, but also the fatty acid compounds formed in the transesterification may be recovered.

From EP-B-0 192 035, there also is known a method for the pre-esterification of free fatty acids in raw fats and/or oils. In this method, in order to reduce the content of free acids in fats and/or oils, these are treated with a low monoalcohol in the presence of acidic esterification catalysts, using as the catalyst solid cation exchanger resins in acidic form and carrying out the removal of the reaction water after the separation of the reaction mixture from the cation exchanger resin.

The method according to the invention presents advantages in particular in the alkali catalyzed transesterification of triglycerides. In this kind of transesterification it is possible, inspite of acidic esterification, to recycle the acid raw product directly and without separation of the acidic catalyst to a transesterification process. Due to the quantity ratios of acid catalyst of the esterification and alkali catalyst of the transesterification, only insignificant modifications of the pH value will occur in the transesterification process. The acid catalyst of the esterification is withdrawn from the process with the glycerol phase. Free fatty acids possibly not yet esterified are also withdrawn as soaps with the glycerol phase. The esters produced at esterification of the fatty acid phase remain in the ester phase. Thus, the yield of the transesterification process can be substantially increased.

PREFERRED EMBODIMENTS OF THE INVENTION

A particularly preferred embodiment of the method according to the invention consists in that the esterified fatty acids, fatty acid salts and/or other fatty acid compounds are added to said different or further reaction mixture, respectively, at a point at which the further transesterification essentially is completed, but the ester phase and the glycerol phase of said different transesterification have not yet separated from each other.

It has been further shown that the method according to the invention can be best carried out in a way that the transesterification is carried out in various, sequential stages, in each stage being formed a fatty acid phase which is esterified and added to a subsequent transesterification stage.

A further, particularly suitable variant of the method according to the invention consists in that the transesterification is carried out in various sequential stages and that the glycerol phases produced in each of the stages are separated and combined, and that from the combined glycerol phases a fatty acid phase is formed which is esterified and fed to said different reaction mixture, in which the further transesterification is carried out.

In the method according to the invention, all the fats and oils of vegetable and animal origin can be transesterified as the triglycerides. As examples are mentioned: rape-seed oil, soy bean oil, sunflower oil, tallow, palm oil and palm fat, castor oil, coconut oil and coconut fat, olive oil, peanut oil, safflower oil, linseed oil, purgative nut oil, cotton seed oil, rice oil, lard. The method according to the invention is suitable for a plurality of starting products of the most varying quality, ranging from vegetable oils in edible oil quality, over unrefined oils, all the way to animal fats or fatty wastes, such as spent hydraulic oils on fat base, as well as spent edible oils.

As the triglycerides, in particular rape-seed oil, soy bean oil and tallow are very suitable, rape-seed oil fatty acid methyl ester, soy bean fatty acid methyl ester and tallow fatty acid methyl ester being produced by the transesterification, if methanol is used as the alcohol.

It has been shown that the method according to the invention is particularly suitable for the transesterification of fats and/or oils of animal or vegetable origin containing free fatty acids. A further preferred variant of the method according to the invention thus consists in that palm oil or palm fat, respectively, is used as the vegetable oil. Palm oil may contain up to 15% of free fatty acids.

A variant of the method according to the invention, which is of interest for reasons of waste economy, consists in that as the triglyceride waste oil and/or waste fat, such as spent edible oil and/or deep-frying fat or spent hydraulic oils on fat base are employed.

As the alcohols for transesterification and/or esterification, alcohols having 1 to 8 carbon atoms, in particular 1 or 2 carbon atoms, are very suitable. As examples are mentioned: methanol, ethanol, propanol, i-propanol, butanol, sec.-butanol, pentanol, hexanol, heptanol and octanol.

The present invention shall be described in more detail in a preferred embodiment by way of the following application example.

EXAMPLE 31,4 g of a fatty acid phase, which was obtained by the alkali transesterification method for the preparation of rapeseed-oil methyl ester from rape-seed by neutralisation of the resulting glycerol phase, described in AT-B 386.222, and had a methanol content of 8,1 mass %, was mixed with 3,3 g of methanol and 0,3 g of concentrated sulfuric acid and refluxed at a temperature of about 85° C. for 2 hours. By the esterification, the fatty acid content of the fatty acid phase could be reduced from 50 mass % to 12,5 mass %. The resulting mixture of esters, fatty acids and sulfuric acid was fed to a reaction mixture of a further transesterification, after the reaction (=alcoholysis) was completed, but still before the phase separation. This second transesterification was carried out under the same conditions as the first transesterification.

By the addition of the esterified fatty acid phase, the yield of methyl ester could be increased. In the transesterification with esterification and recuperation of the fatty acid phase, 100 g of methyl ester (RME) could be obtained from 100 g of rapeseed-oil. Without recycling of the fatty acid phase, the yield was 97 g of RME per 100 g of rapeseed-oil.

Independently from the reaction procedure—with or without recycling of the esterified fatty acid phase—, the resulting methyl ester always had the desired quality.

We claim:

1. A method for the preparation of fatty acid alkyl esters by transesterification, in particular catalytic transesterification, of triglycerides, wherein from a reaction mixture, in which the transesterification is carried out, an ester phase and a glycerol phase containing fatty acids, fatty acid salts or other fatty acid compounds, are formed, which are separated from each other, characterized in that the fatty acids, the fatty acid salts or other fatty acid compounds are separated from the glycerol phase, esterified with an alcohol selected from the group consisting of methanol, ethanol, propanol, i-propanol, butanol, sec.-butanol, pentanol, hexanol, heptanol and octanol and recycled to a different reaction mixture, in which a further transesterification is carried out.

2. A method according to claim 1, characterized in that the esterification is carried out with an acidic catalyst.

3. A method according to claim 2, characterized in that the raw product obtained after esterification with an acid catalyst is added without further treatment to said different reaction mixture.

4. A method according to claim 1, characterized in that the transesterification is carried out under alkali catalysis.

5. A method according to claim 1, characterized in that the esterified fatty acids, fatty acid salts or other fatty acid compounds are added to said different reaction mixture at a point at which the further transesterification is essentially completed, but the ester phase and the glycerol phase of said further transesterification have not yet separated from each other.

6. A method according to claim 1, characterized in that the transesterification is carried out in various sequential stages, in each stage being formed a fatty acid phase which is esterified and added to a subsequent transesterification stage.

7. A method according to claim 1, characterized in that the transesterification is carried out in various sequential stages and that the glycerol phases produced in each of the stages are separated and combined, and that from the combined glycerol phases a fatty acid phase is formed which is esterified and fed to the other reaction mixture, in which the further transesterification is carried out.

8. A method according to claim 1, characterized in that methanol or ethanol is employed as the alcohol for the transesterification and the esterification.

9. A method according to claim 3, characterized in that the transesterification is carried out under alkali catalysis.

10. A method according to claim 4, characterized in that the esterified fatty acids, fatty acid salts or other fatty acid compounds are added to said different reaction mixture at a point at which the further transesterification is essentially completed, but the ester phase and the glycerol phase of said further transesterification have not yet separated from each other.

11. A method according to claim 5, characterized in that the transesterification is carried out in various sequential stages, in each stage being formed a fatty acid phase which is esterified and added to a subsequent transesterification stage.

12. A method according to claim 5, characterized in that the transesterification is carried out in various sequential stages and that the glycerol phases produced in each of the stages are separated and combined, and that from the combined glycerol phases a fatty acid phase is formed which is esterified and fed to the other reaction mixture, in which the further transesterification is carried out.

13. A method according to claim 7, characterized in that methanol or ethanol is employed as the alcohol for the transesterification and the esterification.

\* \* \* \* \*